United States Patent [19]
Bochis et al.

[11] 4,105,767
[45] Aug. 8, 1978

[54] LIMIDAZO[1,2-a] PYRIDINES SUBSTITUTED WITH A THIENYL, THIAZOLYL, OR THIADIAZOLYL GROUP

[75] Inventors: Richard J. Bochis, East Brunswick; Richard L. Tolman, Berkley Heights, both of N.J.

[73] Assignee: Merck & Co., Inc., Rahway, N.J.

[21] Appl. No.: 781,902

[22] Filed: Mar. 28, 1977

[51] Int. Cl.$^2$ .................... A61K 31/44; C07D 471/04
[52] U.S. Cl. ............................. 424/256; 260/294.8 C; 260/295 F; 544/405; 544/238; 544/316
[58] Field of Search ................. 424/256; 260/294.8 C

[56] References Cited
U.S. PATENT DOCUMENTS
4,028,370  6/1977  Irikura .................................. 260/256

*Primary Examiner*—Alan L. Rotman
*Attorney, Agent, or Firm*—David L. Rose

[57] ABSTRACT

Certain novel substituted imidazo [1,2-a] pyridines with a substituted amino group at the 2- or 3- position and a heterocyclic moiety on the pyrido portion of the molecule are active anthelmintic agents. The heterocyclic moiety is connected to the imidazo [1,2-a] pyridine molecule through an oxygen, sulfur, sulfinyl or sulfone. The novel compounds are prepared from the appropriately substituted 2-amino pyridine precursor. Compositions which utilize said novel imidazo [1,2-a] pyridines as the active ingredient thereof for the treatment of helminthiasis are also disclosed.

9 Claims, No Drawings

IMIDAZO[1,2-A] PYRIDINES SUBSTITUTED WITH A THIENYL, THIAZOLYL, OR THIADIAZOLYL GROUP

SUMMARY OF THE INVENTION

This invention is concerned with novel organic compounds classified as imidazo [1,2-a] pyridines which are variously substituted. A loweralkoxycarbonylamino group, optionally substituted with a loweralkyl on the nitrogen is at the 2- or 3-position. A heterocyclic group is connected to the imidazo [1,2-a] pyridine molecule through an oxygen, sulfur, sulfinyl or sulfonyl at any of the available positions on the pyrido portion. Such compounds are active anthelmintic agents. Thus it is an object of this invention to disclose such novel substituted imidazo [1,2-a] pyridines. It is a further object of this invention to disclose processes for the preparation of such compounds. A still further object is to disclose compositions containing such compounds as the active ingredient for the treatment of helminthiasis. Further objects will become apparent upon reading the following Description of the Invention.

DESCRIPTION OF THE INVENTION

The novel substituted imidazo [1,2-a] pyridines of this invention are best realized in the following structure:

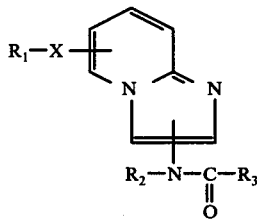

wherein:
X is oxygen sulfur, sulfinyl or sulfonyl;
$R_1$ is a 5- or 6-membered aromatic heterocyclic ring containing from 1 to 4 heteroatoms selected from nitrogen, sulfur and oxygen, which are optionally substituted with a loweralkyl, amino or phenyl group;
$R_2$ is hydrogen or loweralkyl; and
$R_3$ is loweralkoxy.

In the instant application, the following numbering system is employed for the imidazo [1,2-a] pyridine ring system:

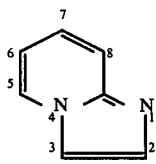

The term "loweralkyl" as employed herein is intended to include those alkyl groups containing from 1 to 6 carbon atoms of either a straight or branched configuration such as methyl, ethyl, propyl, butyl, amyl, hexyl, isopropyl, tert-butyl and the like.

The term "loweralkoxy" as employed herein is intended to include those alkoxy groups containing from 1 to 6 carbon atoms of either a straight or branched configuration such as methoxy, ethoxy, propoxy, amyloxy, hexyloxy, isopropoxy, tert-butoxy and the like.

The 5- or 6-membered aromatic heterocyclic ring containing from 1 to 4 heteroatoms includes, but is not limited to pyridyl, thienyl, thiazolyl, imidazolyl, triazolyl, tetrazolyl, thiadiazolyl, oxazolyl, pyrazinyl, pyrollyl, pyrimidinyl, furyl, and the like.

The foregoing heterocyclic rings may be optionally substituted at any of the available positions with a loweralkyl, amino or phenyl group.

PREFERRED EMBODIMENTS OF THE INVENTION

One aspect of the preferred embodiments of this invention is realized when, in the above structural formula, the loweralkoxy carbonyl group is in the 2-position, and the heterocyclic group is in the 6-position.

Another aspect of the preferred embodiments of this invention is realized when $R_2$ is hydrogen, methyl or ethyl and when $R_3$ is methoxy or ethoxy. In particular, $R_2$ as hydrogen and $R_3$ as methoxy are preferred.

In the preferred embodiments of this invention X is preferred as sulfur (thio) or sulfoxide (sulfinyl).

The preferred heterocyclic groups ($R_1$) of this invention are pyridyl, thienyl, thiazolyl, imidazolyl, thiadiazolyl, thiazolyl, pyridazinyl, pyrimidinyl, and pyrazinyl.

More preferred heterocyclic rings are pyridyl, thienyl, thiazolyl and imidazolyl. Pyridinyl is the most preferred heterocyclic ring. The preferred substituent on the heterocyclic ring is loweralkyl, in particular methyl; however it is most preferred for the heterocyclic ring to be unsubstituted.

Examples of some of the preferred compounds of this invention are as follows:

2-Methoxycarbonylamino-6-(2-pyridylthio) imidazo [1,2-a] pyridine.
2-Methoxycarbonylamino-6-(3-pyridylthio) imidazo [1,2-a] pyridine.
2-Methoxycarbonylamino-6-(4-pyridylthio) imidazo [1,2-a] pyridine.
2-Methoxycarbonylamino-6-(2-pyridylsulfinyl) imidazo [1,2-a] pyridine.
2-Methoxycarbonylamino-6-(2-pyridylsulfonyl) imidazo [1,2-a] pyridine.
2-Methoxycarbonylamino-6-(1-methyl-2-imidazolylthio) imidazo [1,2-a] pyridine.
2-Methoxycarbonylamino-6-(5-methyl-2-thiadiazolylthio) imidazo [1,2-a] pyridine.
2-Methoxycarbonylamino-6-(3-pyridazinylthio) imidazo [1,2-a] pyridine.
2-Methoxycarbonylamino-6-(2-thiazolylthio) imidazo [1,2-a] pyridine.
2-Methoxycarbonylamino-6-(2-pyrimidinylthio) imidazo [1,2-a] pyridine.
2-Methoxycarbonylamino-6-(6-amino-3-pyridylthio) imidazo [1,2-a] pyridine.
2[(methoxycarbonyl)methylamino)-6-(2-pyridylthio)-imidazo [1,2-a] pyridine.
3-Methoxycarbonylamino-6-(2-pyridylthio) imidazo [1,2-a] pyridine.
2-(Methoxycarbonylamino)-5-(2-pyridylthio) imidazo [1,2-a] pyridine.
2-Methoxycarbonylamino-8-(2-pyridylthio) imidazo [1,2-a] pyridine.

The compounds of this invention wherein the loweralkoxycarbonylamino group is in the 2-position of the imidazo [1,2-a] pyridine molecule are prepared by reacting an appropriately substituted 2-amino pyridine according to the following reaction scheme:

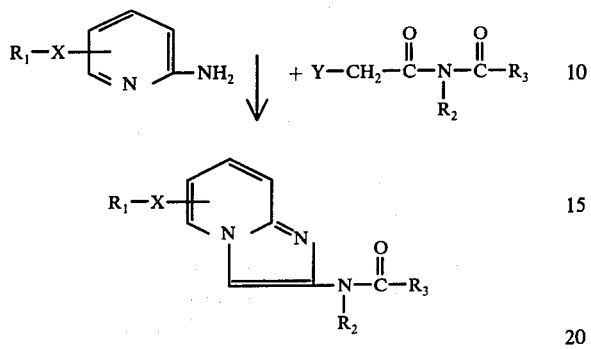

wherein X, $R_1$, $R_2$ and $R_3$ are as previously defined and Y is a halogen selected from chorine, bromine and iodine. The reactants are combined in a solvent which for optimum results should be a polar aprotic solvent. Suitable solvents are: acetonitrile, dimethylformamide, hexemethylphosphoramide, dimethylacetamide, dimethoxyethane and the like. The reaction may be conducted at from 50° to 150° C over a period of from 1 to 50 hours, however it is preferred to heat the reaction at from 75° to 100° C for from 1 to 24 hours. The reaction product is isolated by techniques known to those skilled in this art.

Many of the 2-amino pyridine compounds which are starting materials for the foregoing process are known in the chemical literature. Such compounds, both those known in the art and those not heretofore described, may be prepared according to the following reaction scheme:

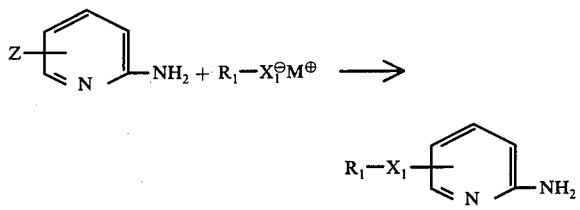

wherein $R_1$ is as previously defined, $X_1$ is oxygen or sulfur, Z is bromine or iodine, and M is an alkali metal.

In the foregoing procedure a bromo or iodo 2-amino pyridine is reacted with an alkali metal salt of a hydroxy or mercapto substituted heterocyclic compound. The reactants are combined in a solvent such as a loweralkanol, dimethylacetamide, N-methyl pyrrolidinone and the like. The reaction is optionally assisted by a catalyst such as powdered copper or cuprous chloride. The reaction mixture is sealed and heated at from 100° to 250° C for from 2 to 48 hours. The product is isolated from the reaction mixture by techniques known to those skilled in this art.

The compounds of this invention wherein the methoxycarbonylamino group is in the 3-position of the imidazo [1,2-a] pyridine molecule are prepared by acylating an appropriately substituted 3-amino compound according to the following reaction scheme:

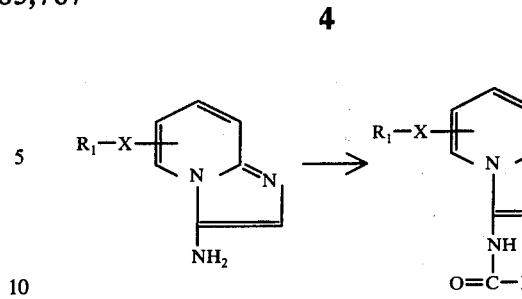

wherein $X_1$, $R_1$, and $R_2$ are as previously defined. The acylation is carried out with appropriately substituted acylating agents such acyl halides, anhydrides, alkylhaloformates and the like. The reaction is generally complete in from 5 minutes to 2 hours at from room temperature to 50° C. In certain cases there is an initial exotherm which will necessitate the application of external cooling. In addition where the reaction process liberates a hydrohalic acid, such as when an acid halide or a haloformate is employed, it is advisable to include in the reaction mixture a single molar equivalent of a base. Inorganic and organic bases may be employed such as alkali metal carbonates or bicarbonates and tertiary amines such as pyridine and triethylamine. The products are isolated using techniques known to those skilled in this art.

The above compounds, wherein the 3-position carbamate amine is unsubstituted are readily converted to the loweralkylated derivatives by alkylation techniques.

Generally the unsubstituted 3-alkoxycarbonylamino compound is converted to a metal salt, preferably an alkali metal salt such as lithium, sodium or potassium, by treatment with a base. Preferred bases are alkali metal hydrides or hydroxides or butyl lithium diisopropylamide. The reaction is generally carried out in an inert solvent such as dimethylformamide, tetrahydrofuran, dimethylsulfoxide and the like, at from room temperature to the reflux temperature of the reaction mixture. Generally, however, a maximum temperature of about 100° C is sufficient. The reaction is generally complete in from 5 minutes to 2 hours.

The metal salt is then treated with an alkyl halide in order to form the N-alkyl substituted compounds. The reaction is generally carried out in the same reaction vessel employed for the preparation of the metal salt. Thus in such cases it is not necessary to isolate the metal salt. The alkyl halide is added directly to the metal salt reaction mixture and the alkylation reaction is generally complete in from 1 to 48 hours at from 0° to 100° C, however, it is preferred to carry out the reaction at room temperature. The alkylated product is isolated using techniques known to those skilled in the art.

The 3-amino-imidazo [1,2-a] pyridine starting materials for the foregoing process are prepared from a halogenated-2-amino pyridine according to the following reaction scheme:

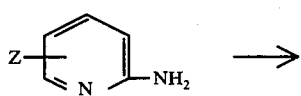

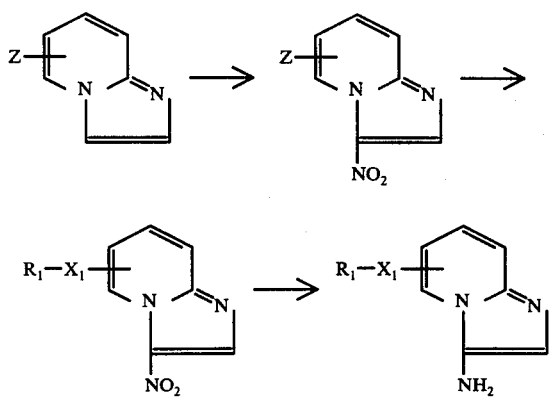

wherein $R_1$, $X_1$, and Z are as previously defined.

In the first step of this process a 2-amino-iodo or bromo pyridine is reacted with a halo acetaldehyde. Generally the haloacetaldehydes are only available as the acetals thereof, in which case, prior to reactions with the 2-amino pyridine compound, it is treated with acid to hydrolize the acetals, leaving the free haloacetaldehyde. A buffer may be added as needed to regulate the pH. The hydrolysis is generally carried out at from 50° C to the reflux temperature and is complete in generally less than one hour. The free haloacetaldehyde is used as soon as possible in the reaction with the 2-amino halo pyridine. The reaction is carried out at from 50° C to reflux temperatures generally in a mixture of an organic solvent and water such as a loweralkanol and water. The reaction is generally complete in from 5 minutes to 2 hours and the product bromo or iodo imidazo [1,2-a] pyridine is isolated using known techniques.

The bromo or iodo compound is then nitrated using standard nitration techniques to prepare the 3-nitro imidazo [1,2-a] pyridine. Preferably a mixture of concentrated nitric and sulfuric acids is employed and the reaction is run at from 0° to 50° C for from 10 minutes to 2 hours. It is generally advisable to maintain the temperature at from 0° to 20° C during the initial period of the reaction, and when the addition is complete to raise the temperature to from 20° to 50° C. The nitrated product is isolated using standard techniques.

The nitrated compound is then reacted with an appropriately substituted metal salt of phenol or thiophenol following the same procedures described above.

The nitro group is then reduced, preferably by catalytic reduction under hydrogen, to the amino compound. The reduction is carried out, preferably at about room temperature, until hydrogen uptake is complete, and the product isolated using techniques known to those skilled in this art.

In addition, the compounds wherein X is sulfur can be converted into the corresponding sulfoxide and sulfone compounds by oxidation. The oxidation reagents used for producing the sulfoxides should be mild reagents such as m-chloroperbenzoic acid and peracetic acid. Further treatment with the mild oxidizing reagent or stronger reagents may be employed for producing the sulfones such as trifluoroperacetic acid, hydrogen peroxide and the like. The oxidation may be carried out on the 2-amino pyridine starting material as well as on the product imidazo [1,2-a] pyridine.

An alternative preparation of the aryl ether of 2-aminopyridine consists of a metal salt of 5-hydroxy-2-methyl pyridine with the appropriate aryl halide in a high boiling polar solvent such as dimethyl formamide or pyridine or even excess aryl halide as solvent. It is helpful to add a small amount of a catalyst such as cuprous bromide. The product, a 5-aryloxy-2-methyl pyridine, is isolated using techniques known to those skilled in the art.

Subsequently the methyl group could be oxidized to a carboxy group with strong oxidizing agents such as selenium dioxide or potassium permanganate. The reaction is generally run in aqueous media at from 50° C to the reflux temperature of the reaction mixture. The carboxylic acid is then converted to the acid halide, preferably the acid chloride with, for example, a thionyl halide, preferably thionyl chloride. The acid halide is then converted to the corresponding azide with alkali metal azide such as sodium azide. The reaction is run at from 0° to 10° C and the azide isolated with known techniques. The azide is solvolitically rearranged, preferably in aqueous acidic media, such as aqueous acetic acid. The resultant 5-phenoxy-2-amino pyridine is isolated and employed to prepare the corresponding imidazo [1,2-a] pyridine.

The best mode contemplated by Applicants for carrying out their invention is set forth in the following examples; it being understood that these examples are for purposes of illustration merely and no limitation is intended except as set forth in the appended claims.

EXAMPLE 1

2-Amino-5-mercapto pyridine

A solution of 19.8 g. (0.09 moles) of 2-amino-5-iodo pyridine and 5.04 g. of sodium hydrogen sulfide in 105 ml. of dimethylformamide is heated at reflux for 16 hours under a nitrogen atmosphere. The reaction mixture is cooled to room temperature and diluted with sufficient ethyl ether to precipitate the product which is collected by filtration. The product is used immediately without further purification in subsequent reactions.

EXAMPLE 2

2-Amino-5-(2-pyridylthio) pyridine 11.0 G. (0.05 moles) of 2-amino-5-iodo pyridine, 6.1 g. (0.055 moles) of 2-mercapto pyridine, 2.97 g. (0.055 moles) of sodium methoxide and 1.0 g. of copper powder are combined in 200 ml. of methanol and heated at 150° C for 12 hours in a glass lined bomb. The reaction mixture is filtered and the filtrate evaporated to dryness in vacuo. The residue is dissolved in 300 ml. of methylenechloride and washed 5 times with 2.5 N sodium hydroxide and 3 times with saturated sodium chloride solution. The methylene chloride is dried over magnesium sulfate, and evaporated to dryness. The residue is dissolved in boiling methanol, treated with decolorizing carbon, filtered and evaporated to dryness affording 2-amino-5-(2-pyridylthio) pyridine, m.p. 121° C.

Using the foregoing procedure, the following compounds are prepared according to the following reaction scheme:

| | R₁ | Weight(A) | Weight(B) | Weight(C) | Weight (Cu) | MP(D) |
|---|---|---|---|---|---|---|
| A | 3-pyridyl | 9.0 g. | 5.0 g. | 2.43 g. | 1.0 g. | 119–123° C |
| B | 4-pyridyl | 11.0 | 6.1 g. | 2.97 g. | 1.0 g. | 129–130° C |
| C | 1-methylimidazol-2-yl | 5.50 g. | 3.42 g. | 1.62 g. | 0.5 g. | 115–120° C |
| D | 5-methyl-1,3,4-thiadiazol-2-yl | 5.50 g. | 3.96 g. | 1.62 g. | 0.5 g. | |
| E | pyridazin-3-yl | 3.27 g. | 2.0 g. | 0.77 g. | 0.21 g. | |
| F | thiazol-2-yl | 10.8 g. | 6.93 g. | 3.19 g. | 0.98 g. | 152–153° C |
| G | pyrimidin-2-yl | 5.0 g. | 3.57 g. | 1.7 g. | 0.5 g. | 159–161° C |
| H | 6-amino-3-pyridyl | 10.2 g. | 5.0 g. | 2.43 g. | 1.0 g. | 251–253° C |

EXAMPLE 3

2-Methoxycarbonylamino-6-(2-pyridylthio) imidazo [1,2-a] pyridine 2.05 G. (0.01 moles of 2-amino-5-(2-pyridylthio) pyridine 1.8 g. (0.012 moles) of methylchloro acetylcarbamate, and 10 ml. of hexamethylphosphoramide are heated under a blanket of nitrogen at 100° C for 4½ hours. A solid forms which is washed 3 times with water and 4 times with methylene chloride. The solid is recrystallized from dimethylformamide/ethanol affording 2-methoxycarbonylamino-6-(2-pyridylthio) imidazo [1,2-a] pyridine, m.p. 230°–236° C.

Using the foregoing procedures, the following compounds are prepared according to the following reaction scheme:

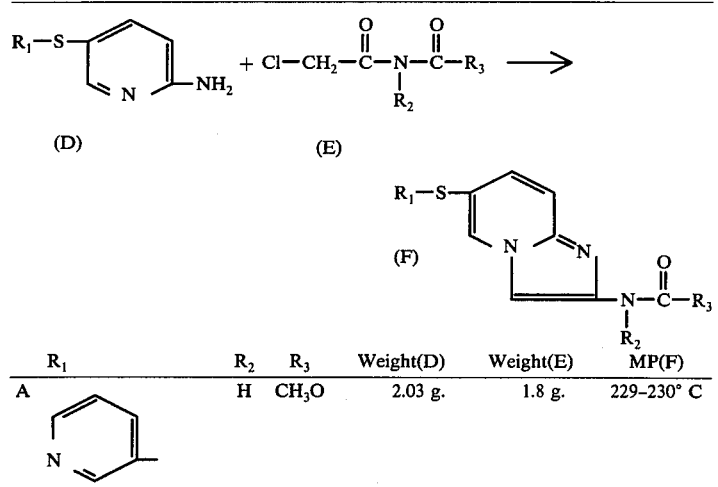

| | R₁ | R₂ | R₃ | Weight(D) | Weight(E) | MP(F) |
|---|---|---|---|---|---|---|
| A | 3-pyridyl | H | CH₃O | 2.03 g. | 1.8 g. | 229–230° C |

-continued

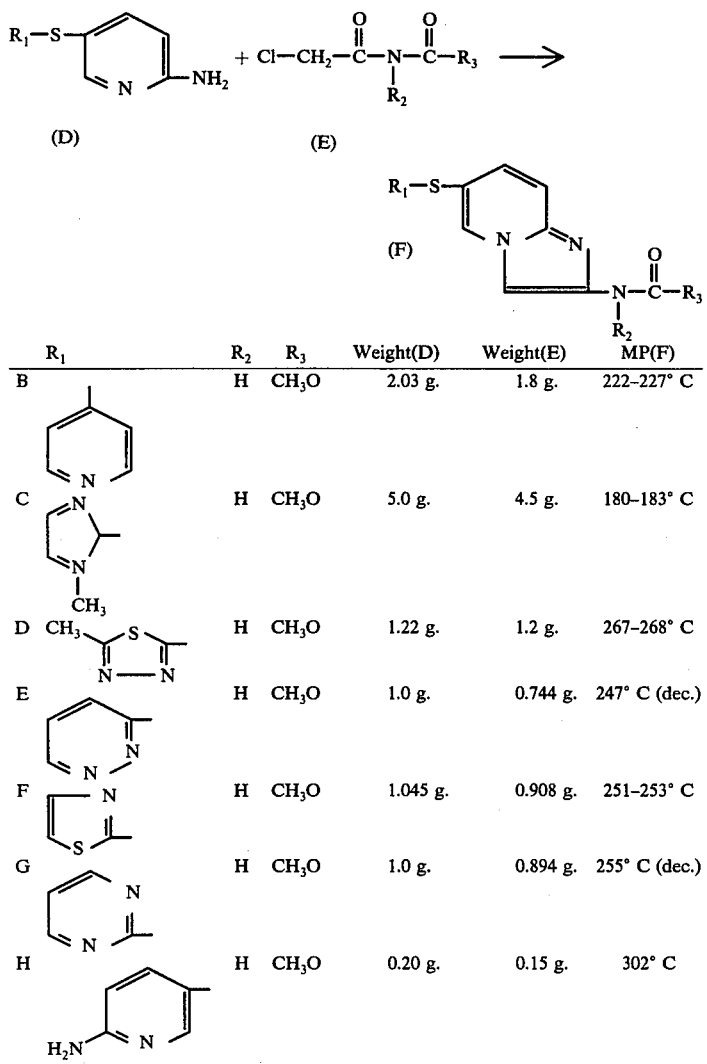

| | $R_1$ | $R_2$ | $R_3$ | Weight(D) | Weight(E) | MP(F) |
|---|---|---|---|---|---|---|
| B | pyridin-4-yl | H | CH₃O | 2.03 g. | 1.8 g. | 222–227° C |
| C | 1-methylimidazolin-2-yl | H | CH₃O | 5.0 g. | 4.5 g. | 180–183° C |
| D | 5-methyl-1,3,4-thiadiazol-2-yl | H | CH₃O | 1.22 g. | 1.2 g. | 267–268° C |
| E | pyridazin-3-yl | H | CH₃O | 1.0 g. | 0.744 g. | 247° C (dec.) |
| F | 1,3-thiazol-2-yl (fused) | H | CH₃O | 1.045 g. | 0.908 g. | 251–253° C |
| G | pyrimidin-2-yl | H | CH₃O | 1.0 g. | 0.894 g. | 255° C (dec.) |
| H | 2-amino-pyridin-5-yl | H | CH₃O | 0.20 g. | 0.15 g. | 302° C |

EXAMPLE 4

2-Methoxycarbonylamino-6-(2-pyridylsulfinyl) imidazo [1,2-a] pyridine

To 0.300 g. (1 mmole) of 2-methoxycarbonylamino-6-(pyridylthio)-imidazo [1,2-a] pyridine in 50 ml. of methylene chloride is added 0.189 g. (1.1 mmoles) of m-chloroperbenzoic acid. The reaction is stirred at room temperature overnight, and the resultant solution is washed 3 times with saturated sodium bicarbonate solution. The methylene chloride layer is dried and evaporated to dryness in vacuo affording 2-methoxycarbonylamino-6-(2-pyridylsulfinyl) imidazo [1,2-a] pyridine, m.p. 231°–235° C.

Following the same procedure as above, using two equivalents of m-chloroperbenzoic acid, there is obtained 2-methoxycarbonylamino-6-(2-pyridylsulfonyl) imidazo [1,2-a] pyridine.

EXAMPLE 5

2[(Methoxycarbonyl)methylamino]-6-(2-pyridylthio)-imidazo [1,2-a] pyridine carbamate A mixture of 2.03 g. (0.01 moles) of 2-amino-5-(2-pyridylthio) pyridine and 2.6 g. (0.015 moles) of N-methylchloroacetyl carbamate in 40 ml. bis-(2-methoxyethyl) ether is heated at reflux for 3 hours. The reaction mixture is cooled, diluted with 400 ml. of water and the resultant precipitate collected by filtration, washed with water and dried. Recrystallization from benzene affords purified 2-[(methoxycarbonyl)methylamino]-6-(2-pyridylthio-imidazo [1,2-a] pyridine.

EXAMPLE 6

2-Amino-5-(2-pyridyloxy) pyridine

A. Sodium salt of 2-methyl-5-hydroxy pyridine

A mixture of 19.25 g. (0.175 mole) of 2-methyl 2-hydroxy pyridine and 9.4 g. (0.175) of sodium methoxide in 500 ml. of pyridine is heated and excess methanol is azeotroped by gentle distillation of approximately 175 ml. of pyridine/methanor mixture.

B. 2-Methyl-5-(2-pyridyloxy) pyridine

To the solution of the sodium phenolate prepared in part A, 19.86 g. 2-chloro pyridine is added. The reaction mixture is heated at 110° C for 16 hours, cooled and filtered. The filtrate is evaporated to dryness in vacuo. The residue is extracted with ether and the ether extracts are washed in 100 ml. of 3N hydrochloric acid. The aqueous layer is separated and made basic with a solution of sodium hydroxide. After extraction with ether, the washed and dried extracts yield 2-methyl-5(2-pyridyloxy) pyridine.

C. 5(2-pyridyloxy) picolinic acid 2.26 G. of 2-methyl-5(2-pyridyloxy) pyridine is suspended in 110 ml. of water and 3.8 g. of potassium permanganate is added. The mixture is heated at 95° C and further 3.8 g. portions of potassium permanganate are added at two hour intervals until a total of 19 g. of permanganate is added (total heating time is 18 hours). The cooled reaction mixture is filtered, and the filtrate is concentrated in vacuo to 50 ml. volume. After extraction of the solution with ether, the pH of the aqueous layer is adjusted to pH 6 and the solution is extracted with ethyl acetate. Evaporation of the combined extracts yields 5(2-pyridyloxy) picolinic acid.

D. 2-Amino 5-(2-pyridyloxy) pyridine 3.13 g. of 5(2-pyridyloxy) picolinic acid is refluxed in 50 ml. of thionyl chloride for 1 hour. The solvents are removed in vacuo and the residue is taken up in benzene and the solvent is once again removed in vacuo. This process is repeated 3 times until all traces of thionyl chloride are removed. The crude acid chloride is dissolved in 30 ml. of acetone and cooled in an ice bath. Dropwise 1.32 g. of sodium azide in 3 ml. of water is added. The reaction mixture is stirred at 0°-5° C for 15 minutes and allowed to stand at room temperature for 15 minutes. After dilution with 120 ml. of water, the crude acylazide is removed by filtration and washed with water. The acylazide is immediately suspended in 60 ml. of 50% aqueous acetic acid and heated at 100° C for 1 hour. The cooled reaction mixture is filtered, basified to pH 8 with 3N sodium hydroxide and extracted with ether, and ethyl acetate. Evaporation of the solvent in vacuo yields 2-amino 5-(2(pyridyloxy) pyridine.

EXAMPLE 7

2-Amino-5-(3-pyridyloxy) pyridine 3.3 G. of potassium 3-pyridinolate, 5.47 g. of 2-amino 5-iodopyridine and 1.78 g. of cuprous oxide in 150 ml. of dimethylacetamide are heated at reflux under a nitrogen atmosphere for 24 hours. The solvent is removed in vacuo and the residue is extracted with chloroform. Chromatography of the methylene chloride soluble portion with silica gel and elution with ethyl acetate yields 2-amino-5-(3-pyridyloxy) pyridine.

EXAMPLE 8

2-(Methoxycarbonylamino)-6-(2-pyridyloxy) imidazo [1,2-a] pyridine

Reaction of 2-amino-5-(2-pyridyloxy) pyridine with methyl chloroacetylcarbamate as in Example 3 yields 2-(methoxycarbonylamino)-6-(2-pyridyloxy) imidazo [1,2-a] pyridine.

EXAMPLE 9

2-(Methoxycarbonylamino)-6-(3-pyridyloxy) imidazo [1,2-a] pyridine

Reaction of 0.372 g. of 2-amino-5(3-pyridyloxy) pyridine and 0.045 g. of methyl chloroacetylcarbamate as in Example 3 yields 2-(methoxycarbonylamino) 6-(3-pyridyloxy) imidazo [1,2-a] pyridine.

EXAMPLE 10

3-(Methoxycarbonylamino) 6-(2-pyridylthio) imidazo [1,2-a] pyridine

A. 6-Bromoimidazo [1,2-a] pyridine

A mixture of 75 ml. of water, 5 ml. of concentrated hydrochloric acid and 30 ml. of chloroacetaldehyde dimethyl acetal is heated at 90° for 10 minutes. After the addition of 20 g. of sodium acetate, the warm solution is poured into a solution of 25 gms. of 2-amino-5-bromopyridine in 160 ml. of 60% ethanol-water containing 10 g. of sodium acetate. The reaction mixture is refluxed for 20 minutes. The ethanol is removed in vacuo and the aqueous suspension is extracted with ethyl acetate. The combined extracts are washed with saturated aqueous sodium chloride. The organic layer is separated and extracted once with 200 ml. of 1N hydrochloric acid. The aqueous layer is separated, made basic with 2.5N sodium hydroxide and extracted with ethyl ether. Evaporation of the dried ether extracts to a small volume yields 11.6 g. of 6-bromoimidazo [1,2-a] pyridine. Further recrystallization from ethyl ether yields purified product m.p. 75°-78.5° C.

B. 3-Nitro-6-bromoimidazo [1,2-a] pyridine

A solution of 24 gms. (.122 mole) of 6-bromoimidazo [1,2-a] pyridine in 80 ml. of concentrated sulfuric acid is treated dropwise with 24 ml. of concentrated nitric acid while maintaining a temperature of 15° C with external cooling. When the addition is complete, the reaction mixture is stirred at room temperature for ½ hour and poured onto 450 gm. of ice. The pH of the mixture is adjusted to pH 4 with aqueous potassium hydroxide and the resultant solids are collected by filtration. The filter cake is washed with water and dried. Recrystallization from methylene chloride-hexane yields pure 3-nitro 6-bromoimidazo [1,2-a] pyridine m.p. 160°-161° C.

C. 3-Nitro-6-(2-pyridylthio) imidazo [1,2-a] pyridine

A solution of 1.61 g. (0.012 mole) of the sodium salt of 2-mercapto pyridine and 2.42 g. (0.01 mole) of 6-bromo-3-nitroimidazo [1,2-a] pyridine in 10 ml. N-methylpyrolidinone is heated at 150° C for 40 minutes under a nitrogen atmosphere. The cooled solution is poured onto 100 ml. of ice-water and the resultant suspension is extracted with ethyl acetate. The combined extracts are washed with saturated aqueous sodium chloride and dried over magnesium sulfate. Evaporation of the solvent to a small volume and dilution with N-hexane yields crystalline material. The solids are purified by chromatography on silica gel. Elution with methylene chloride yields pure 3-nitro 6-(2-pyridylthio) imidazo [1,2-a] pyridine.

D. 3-Amino-6-(2-pyridylthio) imidazo [1,2-a] pyridine

A solution of 0.542 gm. (0.002 mole) of 3-nitro-6-(2-pyridylthio) imidazo [1,2-a] pyridine in 20 ml. of dioxane is reduced at 40 psi. under a hydrogen atmosphere with 0.500 g. of 5% palladium on carbon as catalyst. When the uptake of hydrogen is complete, the catalyst is removed by filtration. The filtrate is evaporated in vacuo to yield 3-amino-6-(2-pyridylthio) imidazo [1,2-a] pyridine.

E. 3-(Methoxycarbonylamino)-6-(2-pyridylthio) imidazo [1,2-a] pyridine

A solution of 1.0 g. of 3-amino-6-(2-pyridylthio) imidazo [1,2-a] pyridine in 25 ml. of chloroform containing 0.401 g. of triethyl amine is treated dropwise with 0.378 g. of methylchloroformate. The reaction mixture is stirred for 3 hours at room temperature. The chloroform is removed in vacuo and the residue is triturated with water. The solids are collected by filtration, washed well with water and dried. Recrystallization from dimethylformamide-ethane yields pure 3-(methoxycarbonylamino) 6-(2-pyridylthio) imidazo [1,2-a] pyridine.

EXAMPLE 11

3-(Methoxycarbonylamino)-6-(2-pyridylsulfinyl) imidazo [1,2-a] pyridine

Oxidation of 3-methylcarbonylamino 6-(phenylthio) imidazo [1,2-a] pyridine using metachloroperbenzoic acid is carried out as in Example 4 affording 3-(methoxycarbonylamino)-6-(2-pyridylsulfinyl) imidazo [1,2-a] pyridine.

EXAMPLE 12

3-(Methoxycarbonylamino)-6-(phenylsulfonyl) imidazo [1,2-a] pyridine

Following the procedure of the second paragraph of Example 4, there is prepared 3-(methoxycarbonylamino)-6-(2-pyridylsulfonyl) imidazo [1,2-a] pyridine.

When the imidazo [1,2-a] pyridines of this invention are employed for the treatment and control of helminthiasis, the specific means employed for administering the imidazo [1,2-a] pyridines to the animal are not critical and any of the methods now used or available for treating animals infected with or susceptible to infection by helminths are satisfactory. Where it is desired to administer the imidazo pyridine in dry, solid unit dosage form, capsules, boluses or tablets containing the desired amount of imidazo pyridine usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of anthelmintic agent depending upon factors such as the type of host animal to be treated, the severity and type of infection and the weight of the host. For large animals such as sheep, swine and cattle, unit dosages up to 15 gm., containing from 3 to 12 gm., of imidazo pyridine, may be employed. It is usually preferred, however, to employ unit dosages weighing from 5 to 10 gm. containing from 2 to 8 gm. of imidazo pyridine. Boluses as well as smaller size tablets contain various binders and lubricants and are compounded by techniques well-known in the art. Capsules are prepared readily by mixing the active ingredient with a diluent such as starch or lactose and filling into the capsule.

In order to treat infected animals by means of a drench, the substituted imidazo pyridines of this invention are mixed with a suspending agent such as bentonite and the solid mix is added to water just prior to administration. Preferred drench formulations contain from about 5 to 50% by weight of the imidazo pyridine.

The imidazopyridine described herein also may be administered as a component of the feed of the animals or may be dissolved or suspended in the drinking water. Such compositions comprise the imidazo pyridine intimately dispersed in an inert carrier of diluent. By inert carrier, is meant one that will not react with the imidazo pyridine and one that may be administered safely to animals. Preferably, the carrier is one that is, or may be, an ingredient of the animal'ration.

Suitable compositions include feed supplements in which the active ingredient is present in relatively large amounts and which are suitable for addition to the feed either directly or after an intermediate dilution of blending step. Typical carrier or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active imidazo pyridines are intimately dispersed throughout the carrier by method such as grinding, stirring, milling or tumbling. Compositions containing from about 5 to 50% by weight of the imidazo pyridines are particularly suitable as feed additives.

Examples of typical feed supplements containing the imidazo pyridines of this invention dispersed in a solid carrier are:

| (A) | Lbs. |
|---|---|
| 2-(Methoxycarbonylamino)-6(2-pyridylthio) imidazo [1,2-a] pyridine | 20 |
| Corn distiller's dried grains | 80 |
| (B) | |
| 2-(Methoxycarbonylamino)-6-(2-pyridylsulfinyl) imidazo [1,2-a] pyridine | 5 |
| Wheat standard middling | 95 |
| (C) | |
| 2-(Methoxycarbonylamino)-6-(3-pyridylthio) imidazo [1,2-a] pyridine | 35 |
| Wheat shorts | 65 |
| (D) | |
| 2-(Methoxycarbonylamino)-6-(4-pyridylthio) imidazo [1,2-a] pyridine | 50 |
| Corn distiller's grains | 50 |

These and similar feed supplements are prepared by uniformly mixing the imidazo pyridine with the carrier.

Such supplements are added to the animal feed in an amount to give the finished feed the concentration of midazo pyridine desired for the treatment and control of helminthiasis. Although the desired concentration of active compounds will vary depending upon the factors previously mentioned as well as upon the particular imidazo pyridine employed, the imidazo pyridine of this invention are usually fed at concentrations of between 0.5 to 2.0% in the feed in order to achieve the desired anthelmintic result.

The imidazopyridines of this invention are also effective fungicides in a variety of applications. Accordingly, they may be employed as fungicides by conventional techniques in the protection of plants, soils, fruits, seeds, fur, wood, paint, textiles, cosmetics, leather, tobacco, rope, paper, pulp, plastic, fuel, rubber, food and the like.

It should be understood that the imidazo pyridine compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired. Thus, it will be appreciated that the imidazo pyridines of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc and the like, or water and various organic liquids such as lower alkanols, for example ethanol and isopropanol or kerosene, benzene, toluene and other petroleum distillate fractions or mixtures thereof. The quantity of active imidazo pyridines contained in such formulations will vary widely depending upon the particular imidazo pyridines employed and the particular application intended. In general, useful formulations will contain from about 1 to about 95% of the active imidazo pyridines.

It should be understood also that the imidazo pyridines of the invention may be used in combination one with the other as well as with other fungicidally active materials. For instance, the imidazo pyridines disclosed above may be mixed with sorbic acid or its salts, propionic acid or its salts, mycostatin, sodium diacetate, trichomycin, amphotercin, griseofluvin, undecylenic acid, chloroquinadol, 5,7-dichloro-8-hydroxyquinoline (Vioform), sodium o-phenylphenate, o-phenylphenol, biphenyl, chlorinated phenols, sodium benzoate, dehydroacetic acid and its salts or esters of parahydroxybenzoic acid, such as the methyl and propyl ester (parabens) to give added fungicidal effect when used in appropriate concentrations. It is quite clear, too, that the imidazo pyridines of this invention may be used in conjunction with effective anti-bacterial materials in appropriate instances so as to combine the action of each in such a situation as to be particularly useful, for instance, in applications where the presence of bacteria creates undesirable results alongside the detrimental action of fungi. Accordingly, a combination of antifungal and antibacterial agents will be useful in the preparation of germicidal soaps, in the production of cosmetics, and in food, such as beer, cheese, or meat and other leather applications.

It has been found that growth of various fungi existing in soil is limited or terminated by the addition to the soil of minor quantities of the imidazo pyridine compounds described. The term soil as used herein is intended to include all media capable of supporting the growth of plants and may include humus, sand, manure, compost, artificially created plant growth solution, and the like. It has been found also that the imidazo pyridines of the invention are effective against fungal diseases of plants and may be effectively used either by direct contact with the foliage or systemically, by introduction through the roots.

The compounds of this invention also have activity against bacteria and plant nematodes and may, at appropriate levels of concentration, be effectively used to inhibit or prevent the growth of these organisms.

As fungicides, the imidazo pyridines of the present invention are useful in inhibiting mold growth in fruit such as citrus fruit. The active agent may be applied at any time before consumption and preferably after harvesting. For instance, the anti-fungal may be applied during initial storage, before or after shipping or during final storage before consumption. The imidazo pyridines may be utilized in a number of ways in this regard and may be applied either directly to the fruit in an emulsion, solution, suspension or the like or it may be applied to the fruit container or wrapper. Suitable carriers for the active agents are waxes and other materials presently known in the art.

What is claimed is:

1. A compound having the formula:

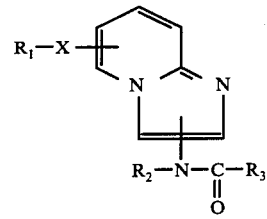

wherein

X is oxygen, thio, sulfinyl or sulfonyl;

$R_1$ is thienyl, thiazolyl or thiadiazolyl, which are optionally substituted with a loweralkyl, amino or phenyl group;

$R_2$ is hydrogen or loweralkyl; and $R_3$ is loweralkoxy.

2. The compound of claim 1 in which the loweralkoxycarbonyl group is in the 2-position and the $R_1$-X-group is in the 6-position of the imidazo [1,2-a] pyridine ring system.

3. The compound of claim 2 wherein $R_2$ is hydrogen, methyl or ethyl; $R_3$ is methoxy or ethoxy; and X is thio or sulfinyl.

4. The compound of claim 3 wherein $R_1$ is thienyl.

5. The compound of claim 3 wherein $R_1$ is thiazolyl.

6. The compound of claim 5 which is 2-methoxycarbonylamino-6-(5-methyl-2-thiadiazolylthio) imidazo [1,2-a] pyridine.

7. The compound of claim 3 wherein $R_1$ is thiadiazolyl.

8. The compound of claim 7 which is 2-methoxycarbonylamino-6-(2-thiazolylthio) imidazo [1,2-a] pyridine.

9. An anthelmintic composition which comprises an inert carrier and a compound having the formula:

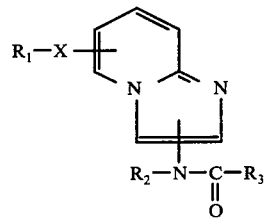

wherein

X is oxygen, thio, sulfinyl or sulfonyl;

$R_1$ is thienyl, thiazolyl or thiadiazolyl, which are optionally substituted with a loweralkyl, amino or phenyl group;

$R_2$ is hydrogen or loweralkyl; and $R_3$ is lower alkoxy.

* * * * *